United States Patent [19]

Schoendorfer et al.

[11] Patent Number: 4,474,568
[45] Date of Patent: Oct. 2, 1984

[54] MULTIPURPOSE COMPONENT CONTAINER AND ANTICOAGULANT BAG

[75] Inventors: Donald W. Schoendorfer, Brookline; Gordon F. Kingsley, Wellesley Hills, both of Mass.

[73] Assignee: Haemonetics Corporation, Braintree, Mass.

[21] Appl. No.: 341,508

[22] Filed: Jan. 21, 1982

[51] Int. Cl.³ .................... A61M 37/00; A61B 19/00
[52] U.S. Cl. ........................................ 604/4; 604/403
[58] Field of Search ............... 210/927; 128/DIG. 24, 128/760; 604/408, 406, 410, 403, 4, 5, 6, 82–85, 262

[56] References Cited

U.S. PATENT DOCUMENTS

| 2,406,207 | 8/1946 | Desmet | 128/214 |
| 2,982,286 | 5/1961 | Welch, Jr. | 128/276 |
| 3,032,037 | 5/1962 | Huber | 128/276 |
| 3,153,414 | 10/1964 | Beall et al. | 128/214 |
| 3,610,226 | 10/1971 | Albisser | 128/760 |
| 3,655,123 | 4/1972 | Judson et al. | 604/6 |
| 3,870,042 | 3/1975 | Viguier | 604/406 |
| 3,896,803 | 7/1975 | Mason | 128/214 |
| 3,945,380 | 3/1976 | Dabney et al. | 604/410 |
| 3,986,506 | 10/1976 | Garber et al. | 604/406 |
| 4,086,924 | 5/1978 | Latham, Jr. | 128/214 |
| 4,146,172 | 3/1979 | Cullis et al. | 233/26 |
| 4,197,847 | 4/1980 | Djerassi | 604/6 |

OTHER PUBLICATIONS

"SRR Lab Introduces New Blood Collection Technology" 10/79.

Primary Examiner—C. Fred Rosenbaum
Assistant Examiner—J. L. Kruter
Attorney, Agent, or Firm—Hamilton, Brook, Smith & Reynolds

[57] ABSTRACT

A multipurpose blood processing bag is described for a system in which anticoagulant and whole blood are mixed outside of the prior art anticoagulated whole blood bag in order to minimize collection lesion. In this system, whole blood and anticoagulant from a multipurpose container are mixed at the phlebotomy needle and the anticoagulated whole blood passed to the anticoagulated whole blood bag. The anticoagulated whole blood may then be separated in a pheresis procedure into components such as plasma or platelets and the separated components stored in the (now empty) multipurpose container.

4 Claims, 3 Drawing Figures

MULTIPURPOSE COMPONENT CONTAINER AND ANTICOAGULANT BAG

DESCRIPTION

1. Technical Field

This invention is in the field of blood donation apparatus.

2. Background Art

In the present state of the art, whole blood is collected, processed and stored in a flexible, thin-walled polyvinyl chloride (PVC) bag called a blood collection bag. In the present state of the art systems, the blood collection bag with a volume of anticoagulant and preservative solutions is coupled in fluid communication by blood compatible tubing with one or more empty component bags. The component bags are used to contain whole blood components such as plasma or platelets separated in a pheresis procedure usually involving centrifugation. The blood collection bag is also coupled in fluid communication by blood compatible tubing with a phlebotomy needle. All of these items, the bags, tubing and needle are sterilized as an entity and are then ready for use as a blood collection set.

After a phlebotomy is made to a donor, the whole blood travels a relatively long distance within the blood compatible tubing before it enters the blood collection bag and the anticoagulant.

There are thus two opportunities for significant damage to be inflicted on the whole blood. The first is in the long journey through the blood compatible tubing while the blood is still un-anticoagulated. The other opportunity for damage occurs when the blood enters the collection bag and is subjected to the entire volume of anticoagulant stored in the bag. This is referred to as "concentration shock". These two areas of damage constitute what is known in the art as the collection lesion.

Co-pending patent applications U.S. patent application Ser. No. 182,510 filed Aug. 29, 1980 now U.S. Pat. No. 4,385,630 issued May 31, 1983 and U.S. patent application Ser. No. 06/256,694 now U.S. Pat. No. 4,425,114, filed Apr. 23, 1981, disclose method and apparatus for whole blood collection where the collection lesion is minimized or totally avoided. Each of the above referenced applications include some means of ratioing a volume of anticoagulant as a function of the volume of whole blood collected. The ratioing is accomplished at a point immediately downstream of the phlebotomy needle.

While the apparatus disclosed in these co-pending applications significantly improve the quality of the whole blood collected by avoiding collection lesion, each of these systems has a disadvantage in that they require an additional container in the blood collection set in order to store the anticoagulant which is being ratioed into the tubing connected to the whole blood bag.

Inasmuch as whole blood collection and component separation is a highly competitive market, the additional expense of this extra bag detracts from the acceptability of these systems.

Accordingly, a need exists for a system and method for ratioing in a volume of anticoagulant as a function of the volume of whole blood collected but which does not require an additional bag for storage of the anticoagulant which is being ratioed.

The solution, proposed in the present invention, is to utilize one of the component bags to store the anticoagulant during blood collection. Thus, during blood collection, the anticoagulant may be taken from this dual purpose bag and after collection the dual purpose bag is used as a component bag.

This solution, however, introduces another complexity, in respect to the system described in co-pending application Ser. No. 06/256,694 now U.S. Pat. No. 4,425,114 referenced above. In that system, the donor supplies the power to pump the blood by squeezing the vacuum pump in the donor's hand. Precise ratioing of anticoagulant is derived by the fact that the whole blood bag and the anticoagulant bag are manufactured to have a specific relationship in surface areas. Specifically, where the desired ratio of anticoagulated whole blood to anticoagulant is 8-1; the surface area of each bag normal to its thickness is designed to have an 8-1 ratio. The problem is to devise a method and apparatus for achieving this 8-1 ratio in surface area for whole blood collection in a component bag which must have a surface area significantly larger than $\frac{1}{8}$th of the whole blood bag.

DISCLOSURE OF THE INVENTION

In a preferred embodiment of the apparatus of this present invention, a dual purpose flexible bag for containing either anticoagulant or separated blood components is provided with two ports. One of these ports is connected to blood compatible tubing which is connected to a Y-junction at the distal side of a phlebotomy needle. The other side of the Y-junction is connected through blood compatible tubing to the inlet port of the whole blood collection bag. The remaining port of the dual purpose bag is connected by blood compatible tubing to an outlet port of the whole blood collection bag or to a second component collection bag which in turn is connected to the whole blood collection bag. The number of collection bags, of course, depends on the number of separations required in a particular system.

When used with the apparatus of co-pending patent application Ser. No. 182,510 now U.S. Pat. No. 4,385,630, above referenced, the dual purpose bag could have a volume capacity of about 100 ml or less. The anticoagulant is pumped from this bag by roller pumps up to the Y-junction at the phlebotomy needle and, at the same time, a roller pump pumps blood from the donor's arm through the phlebotomy needle and into the whole blood collection bag. The anticoagulant is mixed with the whole blood at the phlebotomy needle. After all the anticoagulant is pumped from the dual purpose bag it may then be utilized as a component collection bag.

However, in order to utilize such a system in the apparatus of co-pending patent application Ser. No. 06/256,694 now U.S. Pat. No. 4,425,114, an improvement is required which enables the dual purpose bag to be utilized both as a ratioing source of anticoagulant and as a receptacle for storage of separated component. This is accomplished in general as follows. A vacuum chamber is provided in which the anticoagulated whole blood bag and the collection bag(s) are disposed. The anticoagulated whole blood bag and the dual purpose bag with anticoagulant are separated by a movable rigid plate as previously described in the above referenced patent application Ser. No. 06/256,694 now U.S. Pat. No. 4,425,114. However, a second plate is provided adjacent the long surface of the dual purpose bag containing the anticoagulant. This second plate has an opening which enables the anticoagulant stored in the dual purpose bag to bulge through, and the surface area of the bulge in the bag; which is in contact with the above mentioned movable rigid plate, determines the ratio of anticoagulant which will be forced from the dual purpose bag rather than the total area of the bag as disclosed in the above referenced patent application Ser. No. 06/256,694 now U.S. Pat. No. 4,425,114.

As a result of this improvement, the process previously described in connection with Ser. No. 06/256,694 now U.S. Pat. No. 4,425,114, can be accomplished with one less container.

BEST MODE OF CARRYING OUT THE INVENTION

Figure 1:
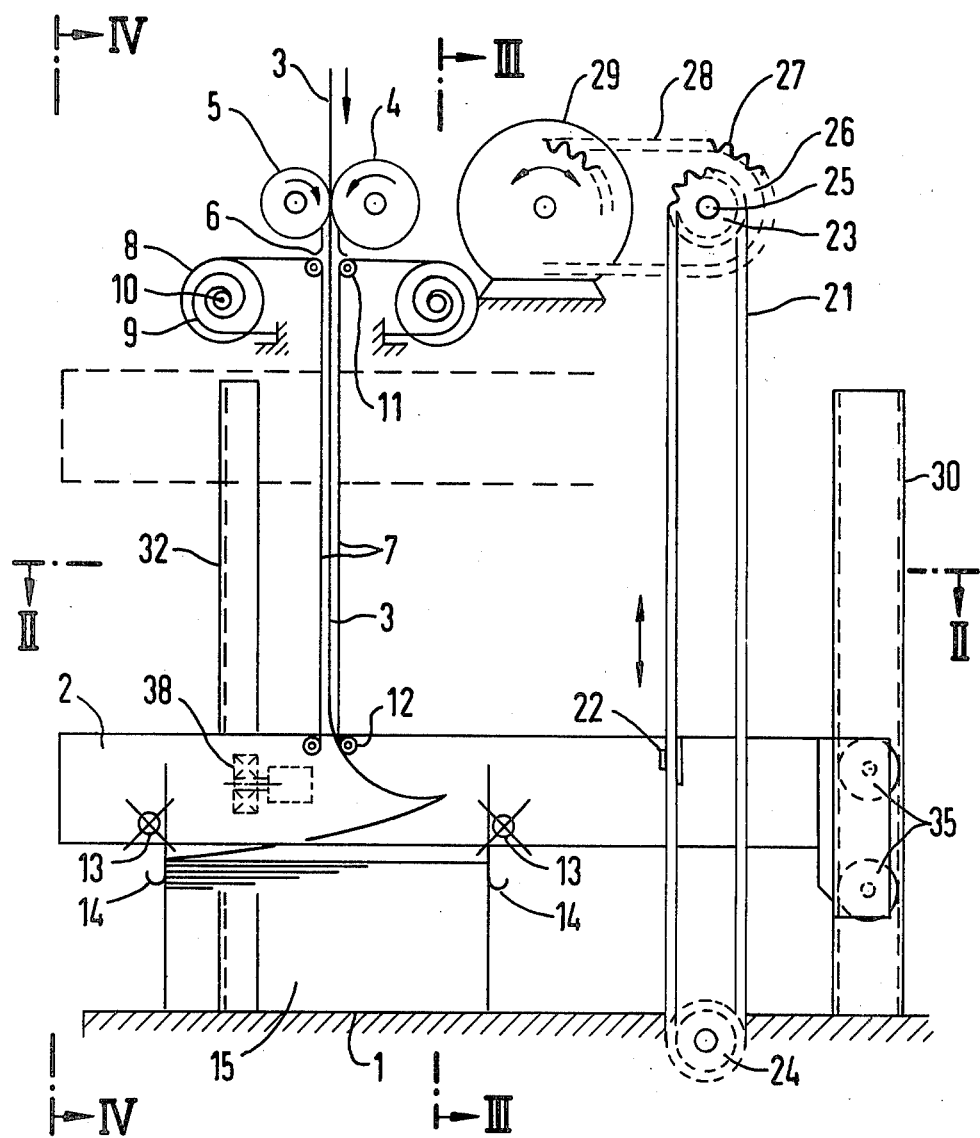
FIG. 1 is a planar view of a whole blood collection set in accordance with the collection.

A preferred embodiment of the invention will now be described in connection with FIGS. 1 through 3. The apparatus comprises an anticoagulated whole blood collection bag 8, a dual purpose (anticoagulant and plasma) bag 4, and a platelet concentrate bag 6.

A phlebotomy needle 14 is connected through blood compatible tubing 34 to Y-connector 36. One port of Y-connector 36 is coupled through blood compatible tubing 21 to the output port of dual purpose bag 4. The other port of Y-connector 36 is connected through blood compatible tubing 20 to an input port of anticoagulated whole blood bag 8. The output port of anticoagulated whole blood bag 8 is coupled through blood compatible tubing to an input port 40 of platelet concentrate bag 6. Conventional slide clamps 38 may be utilized to clamp the tubing during various separation procedures. Access ports 42 may be provided on each of the bags for sampling purposes and other purposes not germain to this invention.

The outlet port of platelet concentrate bag 6 is connected through blood compatible tubing 24 to an inlet port 40 of the dual purpose (anticoagulant and plasma) bag 4.

It may thus be seen that a complete closed circuit is provided from one side of the Y-junction 36 through bag 8 through bag 6 through bag 4 to tubing 21 and to the other side of the Y-junction 36. This collection set may be used as shown in the apparatus described in co-pending application Ser. No. 182,510, wherein the pump that pumps blood from the donor's arm through the phlebotomy needle 14 also pumps anticoagulant from the dual purpose bag 4 through the Y-connector 36 where it mixes with the blood pumped from the donor and flows into the anticoagulated whole blood bag 8 through tubing 20. After the anticoagulant is entirely pumped out of the dual purpose bag 4, this bag may be used as a plasma collection bag in a typical pheresis process, such as, for example, a process described in co-pending U.S. patent application Ser. No. 06/281,655 filed July 9, 1981 now U.S. Pat. No. 4,421,503 and incorporated herein by reference).

In the alternative, it may be desirable to utilize the collection set described in FIG. 1 in connection with a process and apparatus such as previously described in co-pending U.S. patent application Ser. No. 06/256,694 now U.S. Pat. No. 4,425,114. In this embodiment, as can be more clearly seen in FIGS. 2 and 3, a vacuum chamber is provided consisting of a top and bottom section 12 and 11, respectively. The lower section 11 has a stepped cross-sectional portion. The height "h" of this step is just sufficient to accommodate the empty thicknesses of the two component bags 4 and 6. The upper portion of the step is sufficient to accomodate the length of rigid plate 18. Plate 18 is provided with an aperture having an area of a predetermined size. The size of this aperture is sufficient that when chamber 10 is evacuated by pump means (not shown) the anticoagulant which is allowed to bulge through the hole is forced out by rigid plate 16 which abuts the protruding surface of bag 4, adjacent the plate 16. This anticoagulant is mixed with the blood from the donor at Y-junction 36 and coupled through tubing 20 (see FIG. 1) to the anticoagulant whole blood bag 8. A pre-established ratio of anticoagulant is forced out of the dual purpose bag 4 through tubing 21. The ratio is determined, not by the size of the anticoagulant bag, as was the case in the above referenced U.S. patent application 06/256,694 now U.S. Pat. No. 4,425,114, but by the size of the aperture in the lower rigid plate 18.

In other respects the invention operates as described in U.S. patent application 06/256,694 now U.S. Pat. No. 4,425,114 which is incorporated herein by reference.

After the whole blood is anticoagulated and collected in whole blood collection bag and all of the anticoagulant is removed from the dual purpose bag 4, the dual purpose bag 4 may then be utilized as a component collection bag in a pheresis procedure, as described in the above mentioned co-pending patent application U.S. Ser. No. 182,510.

There is thus described a very versatile component collection set whereby a component bag (for example, a platelet component bag or plasma component bag) is also used as the anticoagulant storage bag and in which the ratio of anticoagulant to whole blood is characterized by an element external to the collection set, namely a rigid plate with a hole rather than by a feature incorporated in the bag, namely the size of the bag.

Equivalents

Those skilled in the art will recognize many equivalents to the specific embodiments described herein. Such equivalents are part of this invention and are intended to be covered by the following claims.

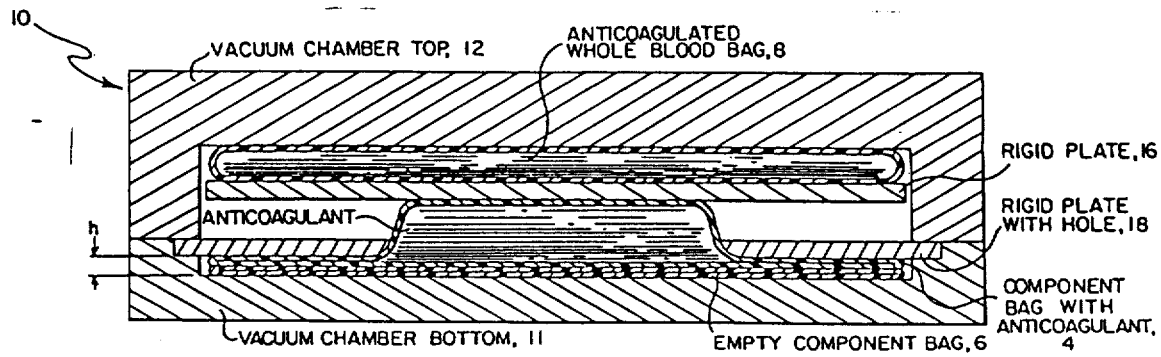

We claim:
1. A blood donation apparatus comprising:
   (a) a first flexible bag means for receiving a first fluid which is a mixture of a second and third fluid, said first flexible bag means having an input port and an output port;
   (b) a second flexible bag means for containing said third fluid, said second flexible bag means having an input port and an output port;
   (c) a source of second fluid;
   (d) a three-port-junction connecting means;
   (e) a first conduit means for coupling the input port of said first flexible bag means to a first port of said three-port-junction connecting means, a second port of said three-port-junction connecting means being connected to the source of said second fluid;

(f) a second conduit means for coupling an output of said second flexible bag means to a third port of said three-port-junction connecting means, and;

(g) a third conduit means for coupling an input port of said second flexible bag means to an output port of said first flexible bag means;

whereby said third fluid and second fluid may be mixed at said three-port-junction connecting means to form said first fluid and whereby said first fluid may be separated into one or more constituent components in said first flexible bag means and a separated component coupled to said second flexible bags means after said third fluid has been removed from said second flexible bag means.

2. The apparatus of claim 1 in which the first fluid is anticoagulated whole blood, the second fluid is whole blood from a donor, and the third fluid is anticoagulant.

3. A blood donor collection apparatus comprising in combination:

(a) a phlebotomy needle;
(b) a first conduit means;
(c) a second conduit means;
(d) a three-port-junction connector means;
(e) a first flexible bag means having an input port and an output port for containing anticoagulated whole blood said input port being connected to one end of the first conduit means;
(f) a second flexible bag means, having an input port and an output port, for initially containing anticoagulant, said output port being connected to one end of the second conduit means;
(g) the remaining ends of said first and second conduit means being fluidly coupled to respective individual ports of the three-port-junction connector means, the remaining port of which is connected to the phlebotomy needle;
(h) a third conduit means fluidly connecting the outport port of said first flexible bag means to the input port of said second flexible bag means said third conduit means comprising a third flexible bag means having an input port and an output port and tubing means fluidly coupling the output port of the third flexible bag means to the input port of the second flexible bag means and the output port of the first flexible bag means to the input port of the third flexible bag means.

4. An evacuated chamber containing a blood donor collection apparatus comprising in combination:

(a) a phlebotomy needle;
(b) a first conduit means;
(c) a second conduit means;
(d) a three-port-junction connector means;
(e) a first flexible bag means, having an input port means and an output port means for containing anticoagulated whole blood said input port means being connected to one end of the first conduit means;
(f) a second flexible bag means, having an input port means and an output port means, for initially containing anticoagulant, said output port means being connected to one end of the second conduit means;
(g) the remaining ends of said first and second conduits means extending from said chamber and being coupled to respective individual port means of the three-port-junction connector means, the remaining port means being fluidly coupled to the phlebotomy needle;
(h) a third conduit means for connecting the output port means of said first flexible bag means to an input port means of said second flexible bag means.

* * * * *

UNITED STATES PATENT AND TRADEMARK OFFICE
CERTIFICATE OF CORRECTION

PATENT NO. : 4,474,568

DATED : October 2, 1984

INVENTOR(S) : Donald W. Schoendorfer et al

Page 1 of 4

It is certified that error appears in the above-identified patent and that said Letters Patent is hereby corrected as shown below:

Title page - (57): After "Abstract" insert -- of the Disclosure --.

The title page should be deleted to appear as per attached title page.

Figure 2:
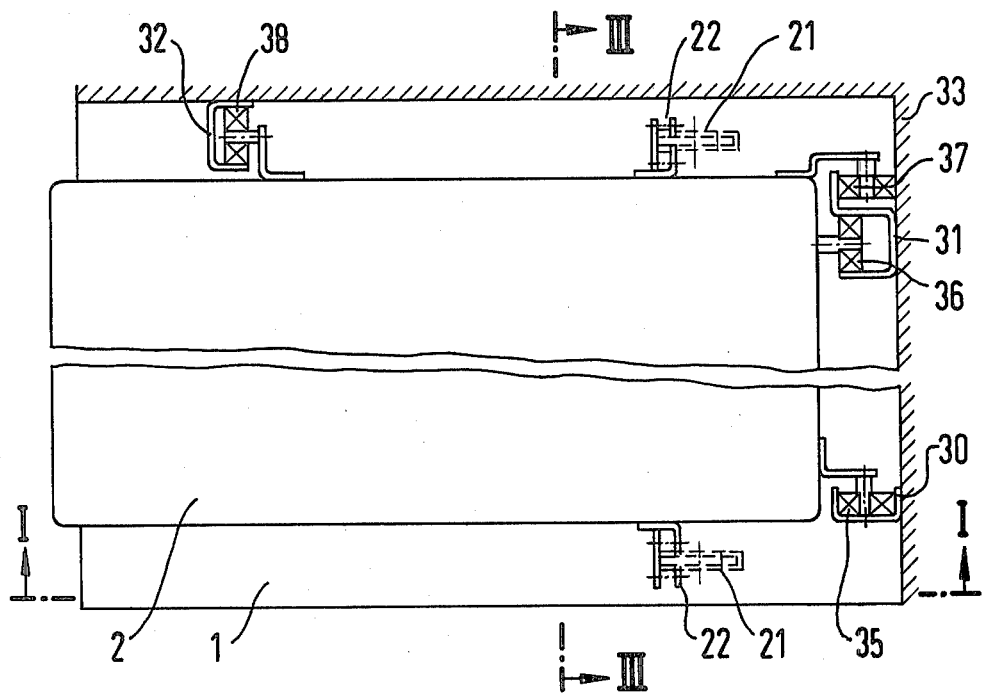
FIG. 2 is an exploded perspective view of a blood donor chamber and collection set in accordance with the invention.
Figure 3:
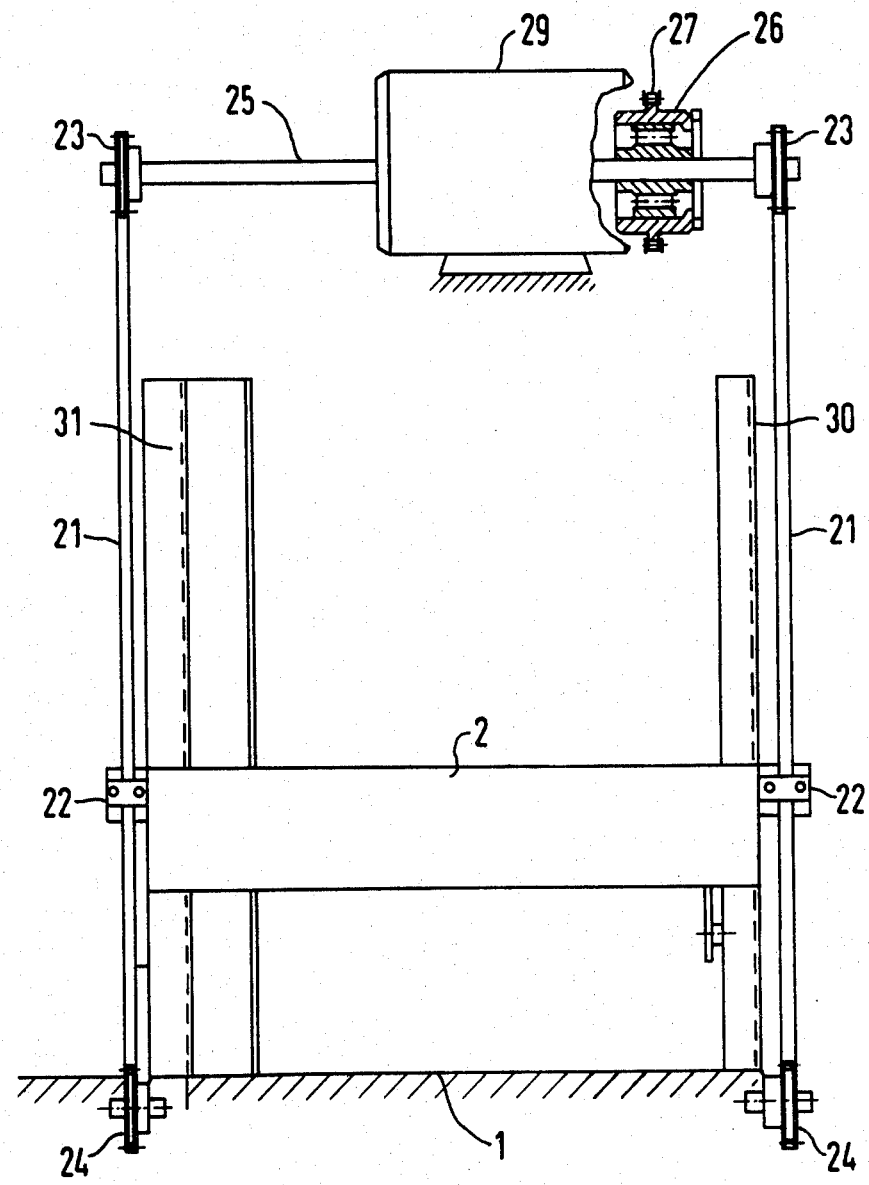
FIG. 3 is a cross-sectional view of a blood donor chamber and collection set of the invention.
Figure 4:
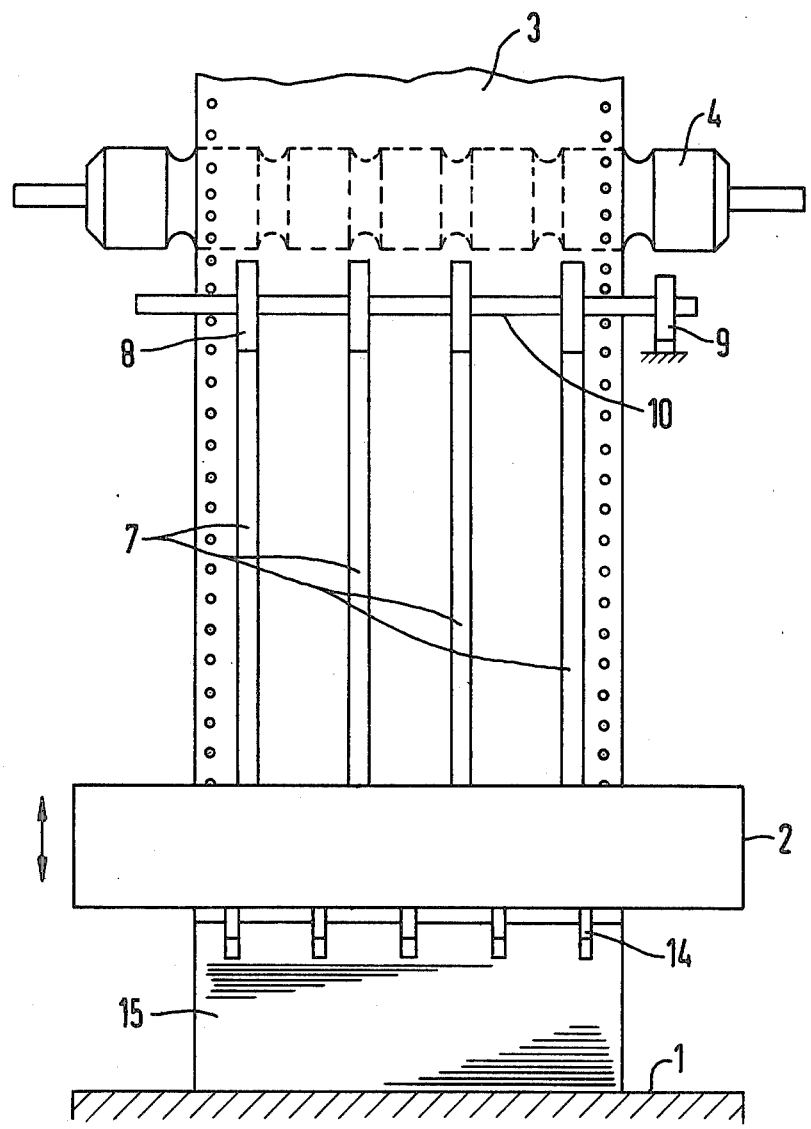
Figure 1:
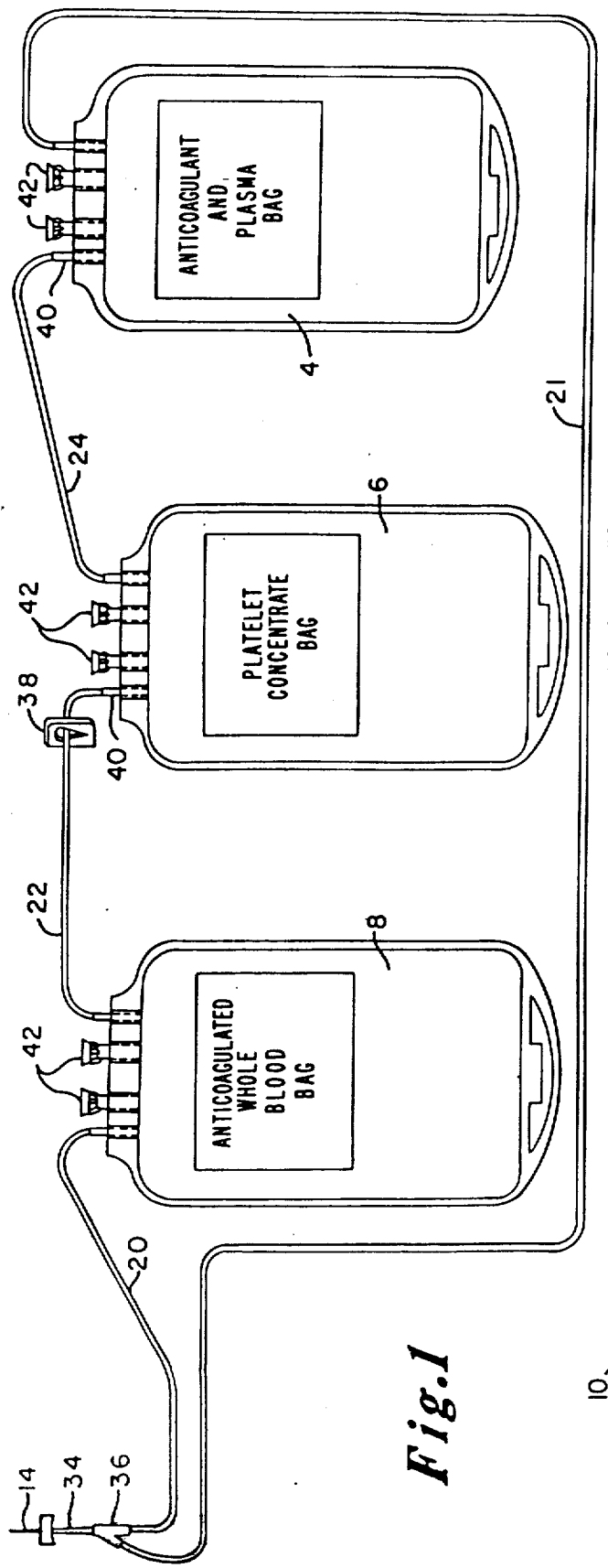
Figure 3:
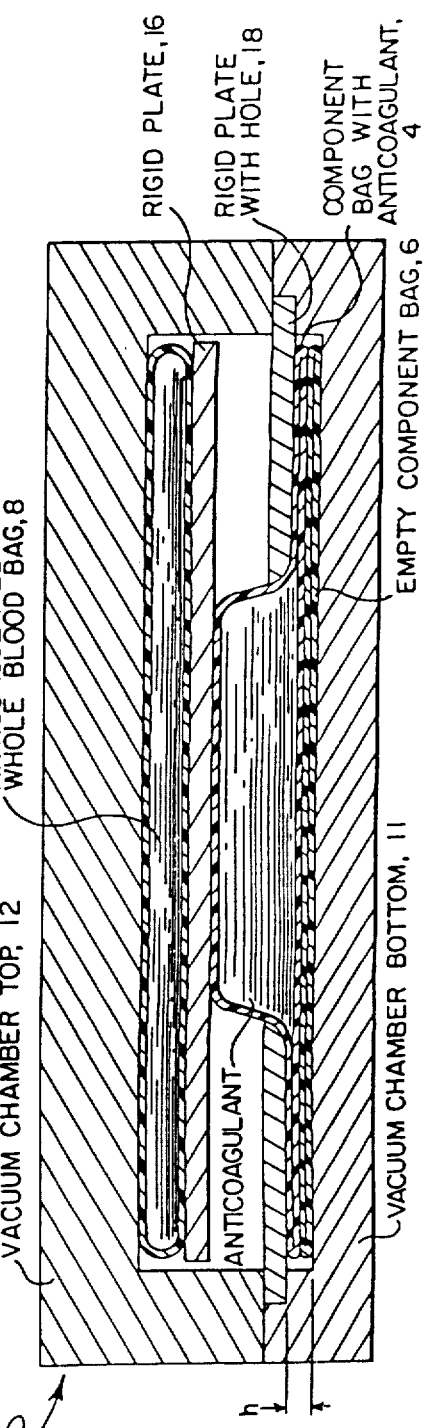
Figure 2:
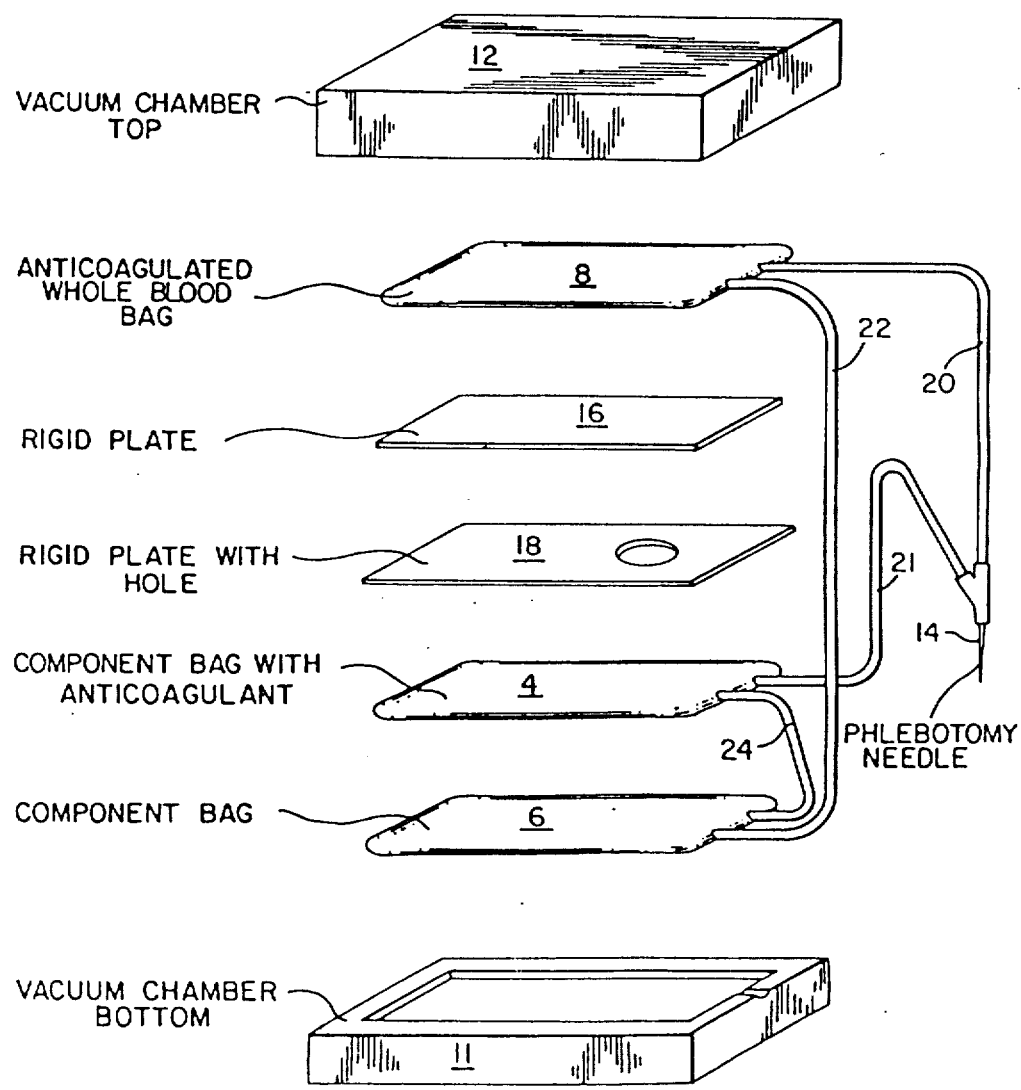

The sheets of drawings containing figures 1-3 should be deleted to be replaced with figures 1-3 as shown on the attached sheet.

Signed and Sealed this

Third Day of September 1985

[SEAL]

*Attest:*

DONALD J. QUIGG

*Attesting Officer*  Acting Commissioner of Patents and Trademarks - Designate

United States Patent [19]

Schoendorfer et al.

[11] Patent Number: 4,474,568
[45] Date of Patent: Oct. 2, 1984

[54] MULTIPURPOSE COMPONENT CONTAINER AND ANTICOAGULANT BAG

[75] Inventors: Donald W. Schoendorfer, Brookline; Gordon F. Kingsley, Wellesley Hills, both of Mass.

[73] Assignee: Haemonetics Corporation, Braintree, Mass.

[21] Appl. No.: 341,508

[22] Filed: Jan. 21, 1982

[51] Int. Cl.³ .................. A61M 37/00; A61B 19/00
[52] U.S. Cl. ............................................. 604/4; 604/403
[58] Field of Search ............... 210/927; 128/DIG. 24, 128/760; 604/408, 406, 410, 403, 4, 5, 6, 82-85, 262

[56] References Cited

U.S. PATENT DOCUMENTS

| | | | |
|---|---|---|---|
| 2,406,207 | 8/1946 | Desmet | 128/214 |
| 2,982,286 | 5/1961 | Welch, Jr. | 128/276 |
| 3,032,037 | 5/1962 | Huber | 128/276 |
| 3,153,414 | 10/1964 | Beall et al. | 128/214 |
| 3,610,226 | 10/1971 | Albisser | 128/760 |
| 3,655,123 | 4/1972 | Judson et al. | 604/6 |
| 3,870,042 | 3/1975 | Viguier | 604/406 |
| 3,896,803 | 7/1975 | Mason | 128/214 |
| 3,945,380 | 3/1976 | Dabney et al. | 604/410 |
| 3,986,506 | 10/1976 | Garber et al. | 604/406 |
| 4,086,924 | 5/1978 | Latham, Jr. | 128/214 |
| 4,146,172 | 3/1979 | Cullis et al. | 233/26 |
| 4,197,847 | 4/1980 | Djerassi | 604/6 |

OTHER PUBLICATIONS

"SRR Lab Introduces New Blood Collection Technology" 10/79.

Primary Examiner—C. Fred Rosenbaum
Assistant Examiner—J. L. Kruter
Attorney, Agent, or Firm—Hamilton, Brook, Smith & Reynolds

[57] ABSTRACT

A multipurpose blood processing bag is described for a system in which anticoagulant and whole blood are mixed outside of the prior art anticoagulated whole blood bag in order to minimize collection lesion. In this system, whole blood and anticoagulant from a multipurpose container are mixed at the phlebotomy needle and the anticoagulated whole blood passed to the anticoagulated whole blood bag. The anticoagulated whole blood may then be separated in a pheresis procedure into components such as plasma or platelets and the separated components stored in the (now empty) multipurpose container.

4 Claims, 3 Drawing Figures